(12) United States Patent
Schiller (10) Patent No.: US 10,028,338 B1
(45) Date of Patent: Jul. 17, 2018

(54) ELECTRODE TORQUE LIFT

(71) Applicant: Contractors & Industrial Supply Company, Inc., Nashville, TN (US)

(72) Inventor: Tom D. Schiller, Franklin, TN (US)

(73) Assignee: Contractors & Industrial Supply Company, Inc., Nashville, TN (US)

( * ) Notice: Subject to any disclaimer, the term of this patent is extended or adjusted under 35 U.S.C. 154(b) by 158 days.

(21) Appl. No.: 14/693,862

(22) Filed: Apr. 22, 2015

Related U.S. Application Data (60) Provisional application No. 61/982,337, filed on Apr. 22, 2014.

(51) Int. Cl.
*H05B 7/14* (2006.01)

(52) U.S. Cl.
CPC ..................................... *H05B 7/14* (2013.01)

(58) Field of Classification Search
CPC ...... B23K 9/028; B23K 9/133; B23K 9/1336; B23K 9/16; B23K 9/164; H05B 7/14
See application file for complete search history.

(56) References Cited

U.S. PATENT DOCUMENTS

| | | | |
|---|---|---|---|
| 2,226,652 A | 12/1940 | York | |
| 2,494,775 A | 1/1950 | Moore | |
| 3,249,673 A | 5/1966 | Moore | |
| 3,517,954 A | 6/1970 | Snyder et al. | |
| 3,600,031 A | 8/1971 | Coleman et al. | |
| 3,752,896 A | 8/1973 | Zimmermann et al. | |
| 3,781,449 A | 12/1973 | Wolf et al. | |
| 3,790,204 A | 2/1974 | Lighthipe, Jr. et al. | |
| 3,796,818 A | 3/1974 | Yuasa et al. | |
| 3,814,828 A | 6/1974 | Gazda | |
| 4,044,199 A * | 8/1977 | Simon | H05B 7/14 373/92 |
| 4,154,974 A | 5/1979 | Wynne | |
| 4,162,368 A | 7/1979 | Brazier | |

(Continued)

FOREIGN PATENT DOCUMENTS

| | | |
|---|---|---|
| IT | 1052996 B | 8/1981 |
| IT | 1192885 B | 5/1988 |

(Continued)

OTHER PUBLICATIONS

U.S. Appl. No. 14/693,652, filed Apr. 22, 2015, Schiller.

(Continued)

*Primary Examiner* — Carl Arbes
(74) *Attorney, Agent, or Firm* — Waller Lansden Dortch & Davis, LLP; Matthew C. Cox (57) ABSTRACT

An electrode joining apparatus for joining a first electrode and a second electrode includes an electrode holder configured to receive the first electrode and a torque device positioned above the electrode holder. The torque device is configured to engage and rotate the second electrode relative to the first electrode. A lift is disposed on the apparatus to move the torque device relative to the electrode holder. In some embodiments, the lift includes a mechanism such as a powered actuator operable to raise the torque device above the electrode holder. In additional embodiments, the lift includes a carriage that is vertically moveable relative to the electrode holder, and the torque device is attached to the carriage.

6 Claims, 10 Drawing Sheets

(56) References Cited

U.S. PATENT DOCUMENTS

| | | | |
|---|---|---|---|
| 4,167,643 A * | 9/1979 | Charnock | H05B 7/14 373/91 |
| 4,185,158 A | 1/1980 | Koga et al. | |
| 4,317,951 A | 3/1982 | Boudeau et al. | |
| 4,323,717 A | 4/1982 | Garner et al. | |
| 4,400,815 A | 8/1983 | Dunn et al. | |
| 4,420,838 A | 12/1983 | Dunn et al. | |
| 4,665,530 A | 5/1987 | Corbethau | |
| 4,703,492 A | 10/1987 | Sekiguchi et al. | |
| 4,736,384 A * | 4/1988 | Sakai | H05B 7/14 373/92 |
| 5,161,845 A | 11/1992 | Carpenter, Jr. | |
| 5,208,442 A * | 5/1993 | Ahola | H05H 1/38 219/121.48 |
| 5,255,285 A | 10/1993 | Aberl et al. | |
| 5,638,398 A | 6/1997 | Ikitsu et al. | |
| 5,757,841 A * | 5/1998 | Ikitsu | B23P 19/105 29/705 |
| 5,870,424 A | 2/1999 | Todoriki et al. | |
| 6,084,200 A * | 7/2000 | Ahola | B23K 10/00 219/121.36 |
| 6,167,076 A | 12/2000 | Ignacio | |
| 6,265,690 B1 * | 7/2001 | Fornsel | B05D 3/144 219/121.39 |
| 7,547,861 B2 * | 6/2009 | Jorgensen | H05H 1/34 164/46 |
| 7,660,337 B2 | 2/2010 | Teeples et al. | |
| 7,992,634 B2 | 8/2011 | Angelle et al. | |
| 9,383,278 B1 | 7/2016 | Schiller | |
| 2008/0084907 A1 | 4/2008 | Lehr et al. | |
| 2010/0272146 A1 | 10/2010 | Piccardi | |
| 2011/0089617 A1 | 4/2011 | Reali et al. | |
| 2011/0274137 A9 | 11/2011 | Piccardi | |
| 2015/0233195 A1 | 8/2015 | Smith et al. | |

FOREIGN PATENT DOCUMENTS

| | | | |
|---|---|---|---|
| IT | 1297835 A1 | | 8/1998 |
| JP | 3388329 | * | 3/2003 |

OTHER PUBLICATIONS

U.S. Appl. No. 14/693,673, filed Apr. 22, 2014, Schiller
U.S. Appl. No. 14/796,964, filed Jul. 10, 2015, Schiller.
U.S. Appl. No. 15/146,877, filed May 4, 2016, Schiller.
U.S. Appl. No. 15/198,949, filed Jun. 30, 2016, Schiller.

* cited by examiner

ELECTRODE TORQUE LIFT

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application is a non-provisional of U.S. Provisional Patent Application Ser. No. 61/982,337 filed Apr. 22, 2014 entitled Electrode Joining Apparatus and Methods, which is herein incorporated by reference in its entirety.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present invention relates generally to machinery for manipulating electrodes and more particularly to devices and methods for joining graphite electrodes for use with metal arc furnaces.

Metal arc furnaces include large vessels for melting metal. Heat may be generated inside the furnaces using graphite electrodes across which electric current is passed. Heat is generated inside the furnace due to a high voltage arc formed by the current passing through one or more electrodes. The heat is used to melt metal.

During use, graphite electrodes are consumed within the furnace vessel, requiring electrodes to be replaced over time. As electrode material is consumed in the furnace, the electrode is shortened to a length where it is no longer independently usable. However, a partially-consumed electrode may be joined to a second partially-consumed or complete electrode to form a joined electrode that can be used. Thus, the partially-consumed electrode may still be useful when placed in combination with a second electrode portion.

Electrodes may be joined in an end-to-end configuration using a threaded joint in some applications. When electrodes are combined, electrical conductivity is generally maintained across the joint, and electricity may be passed from one electrode to the second in the joint electrode. A threaded joint is commonly used to join electrodes. The joining procedure requires at least one electrode to be rotated relative to a second electrode such that a threaded engagement occurs.

The joining process typically requires two stages. During a first stage, the first electrode is rotated relative to the second electrode to allow loose engagement of the corresponding threads. Rotation during this stage encounters relatively little resistance as the threads are rotating. This may be referred to as a spin-down rotation when a free electrode is spun about its longitudinal axis relative to a fixed electrode below the free electrode, to allow the threads to engage.

Before use, the threaded electrode joint must be tightened to a predetermined manufacturer's suggested torque value. A second stage of electrode joining occurs when the end walls of the two electrodes or other structures make contact, requiring greater force to torque the first electrode relative to the second electrode. During this stage, the torque applied generally increases as a function of angular position. This second stage may be referred to as a torque stage. Once a desired torque value, or a value within a desired torque range, is reached, force application is ceased and the electrodes are properly joined.

An improper torque application can damage threads, reduce electrical connectivity between the electrode sections, or cause failure of the joint. Such failure may be catastrophic where the separate electrode sections each weigh several hundred or even several thousand pounds. Because joined electrodes are typically moved inside an industrial setting using overhead transport rigging, joint failure can cause one or both electrode sections to crash down on equipment or workers, causing major damage or injury.

Conventional tools and methods for joining electrodes in a threaded joint include manually rotating one free electrode relative to a fixed electrode. This may be achieved using a manual wrench or other tool for grasping and rotating the free electrode. The applied torque may be measured manually using a torque gauge or manual torque wrench. The conventional manual joining technique is time-consuming for workers and may be dangerous in some applications due to the requirement that a worker be near the additional electrode operating the wrench. Additionally, manual procedures lead to variance in applied torque values as workers may not apply the same torque every time.

Others have attempted to solve the problems associated with manual joining of threaded electrodes by providing devices to assist in the torque application process. For example, U.S. Pat. No. 6,167,076 titled Electrode Wrench provides an apparatus for joining a threaded free electrode section with a threaded fixed electrode section for use in electric arc furnaces. The apparatus includes a driver and a plurality of pawls to grip the free electrode and turn it in one angular direction. The electrode wrench includes a pneumatic cylinder to apply torque against the free electrode in the second stage of joining. During use, a user may measure the pressure applied in the pneumatic cylinder and correlate the pressure to a range of torque values. Thus, a user may stop applying force once a pressure value corresponding to a desired torque range is reached. However, the electrode wrench typically does not provide independent verification, or feedback measurement of applied torque. The failure of such independent verification can lead to improper torque application on the free electrode and the undesirable and dangerous problems mentioned above.

Another problem encountered when joining electrodes includes vertical positioning of the fixed electrode in the torque device such that the grippers in the torque device are aligned to engage the lower end of the free electrode being added from above. If the fixed electrode protrudes from the top of the torque device, the grippers inside the torque device will not be able to engage the free electrode. Conventional torque devices typically are not vertically adjustable relative to the electrode holder, and thus great care must be taken to be sure the top end of the fixed electrode is recessed in the torque device to allow space for the lower end of the free electrode to be positioned for engagement by the grippers. This may lead to difficulty in placing the fixed electrode using some electrode transport machinery. What is needed, then, are improvements in electrode joining devices and methods.

What is needed then are electrode joining devices with improved feedback torque detection.

BRIEF SUMMARY

One aspect of the present disclosure provides an electrode joining apparatus for joining a first electrode and a second electrode including an electrode holder configured to receive the first electrode and a torque device positioned above the electrode holder. The torque device is configured to engage and rotate the second electrode relative to the first electrode during an electrode joining procedure. A lift is disposed on the apparatus to move the torque device relative to the electrode holder. In some embodiments, the lift includes a powered mechanism such as an actuator that raises the torque device above the electrode holder. In additional embodiments, the lift includes a carriage that is vertically moveable relative to the electrode holder, and the torque device is attached to the carriage. The carriage may be moveable along a mast or other structure such as a rail or tower.

Numerous other objects, advantages and features of the present disclosure will be readily apparent to those of skill in the art upon a review of the following drawings and description of a preferred embodiment.

DETAILED DESCRIPTION

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

As described herein, an upright position is considered to be the position of apparatus components while in proper operation or in a natural resting position as described herein. Vertical, horizontal, above, below, side, top, bottom and other orientation terms are described with respect to this upright position during operation unless otherwise specified. The term "when" is used to specify orientation for relative positions of components, not as a temporal limitation of the claims or apparatus described and claimed herein unless otherwise specified. The term "lateral" denotes a side to side direction when facing the "front" of an object.

The phrase "in one embodiment," as used herein does not necessarily refer to the same embodiment, although it may. Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the apparatuses and/or methods disclosed and claimed herein may be made and/or executed without undue experimentation in light of the present disclosure. While the apparatuses and methods of this invention have been described in terms of the embodiments included herein, it will be apparent to those of ordinary skill in the art that variations may be applied to the apparatuses and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Figure 1:
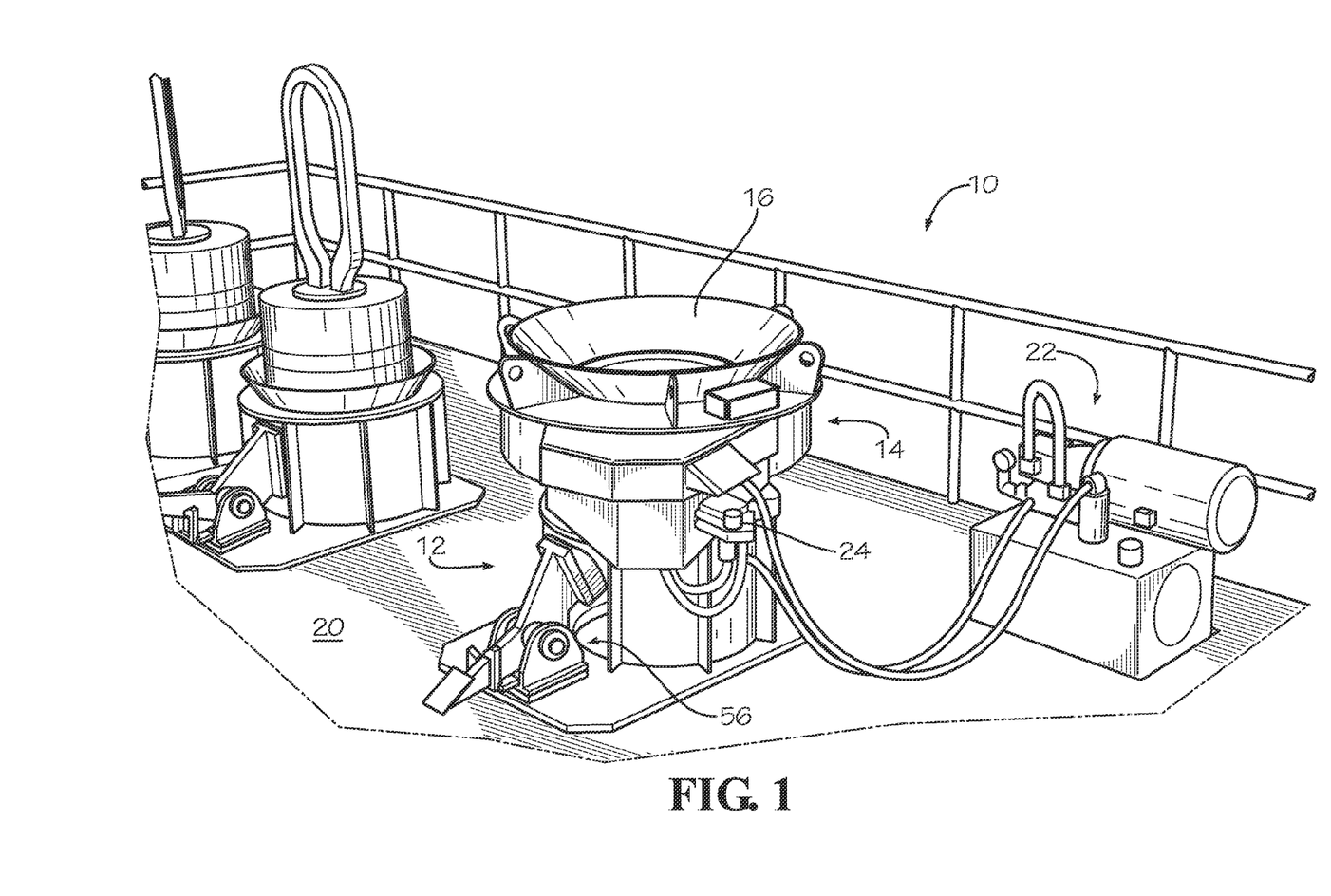
FIG. 1 is a perspective view of an embodiment of an electrode joining apparatus.

Referring now to the drawings, the figures illustrate devices and methods for joining electrodes. As seen in FIG. 1, an electrode joining apparatus 10 includes an electrode holder 12 and a torque device 14 positioned above the electrode holder 12. The apparatus is positioned on a platform 20 where operators may walk. A hole 56 is defined in the platform below the electrode holder 12 to allow passage of an electrode through the joining apparatus and through the platform 20. The torque device 14 includes funnel 16 through which the lower end of an electrode may be installed from above. An axial passage extends through the torque device 14 and through the electrode holder 12 to allow passage of the electrode.

Torque device 14 includes machinery to rotate a free electrode lowered into the funnel 16. The machinery on torque device 14 is generally capable of gripping the lower end of a free electrode and applying a rotational force. The machinery may engage the electrode for both stages of rotation, including the spin-down stage and the torque application stage in some embodiments. In other embodiments, torque device 14 may only apply force during the torque stage.

In some embodiments, the machinery in the torque device 14 responsible for applying force against the free electrode is powered by a mechanical actuator such as a pneumatic or a hydraulic system. For example, as seen in FIG. 1, a hydraulic pump 22 powers a hydraulic motor housed within the drive mechanism 18. Pump 22 is coupled to a drive assembly in torque device 14 to actuate or disengage one or more grippers which extend inwardly in the axial passage on the torque device 14 to rotate the free electrode.

A control 24 allows regulation of applied hydraulic fluid for a hydraulic motor drive or compressed gas for a pneumatic motor drive on torque device 14 in some embodiments. Control 24 includes an electrical control in various embodiments. The control may be used to initiate the spin-down of the free electrode during use. For example, when a free electrode is placed in position, the control may be actuated to start rotating the free electrode.

Figure 2:
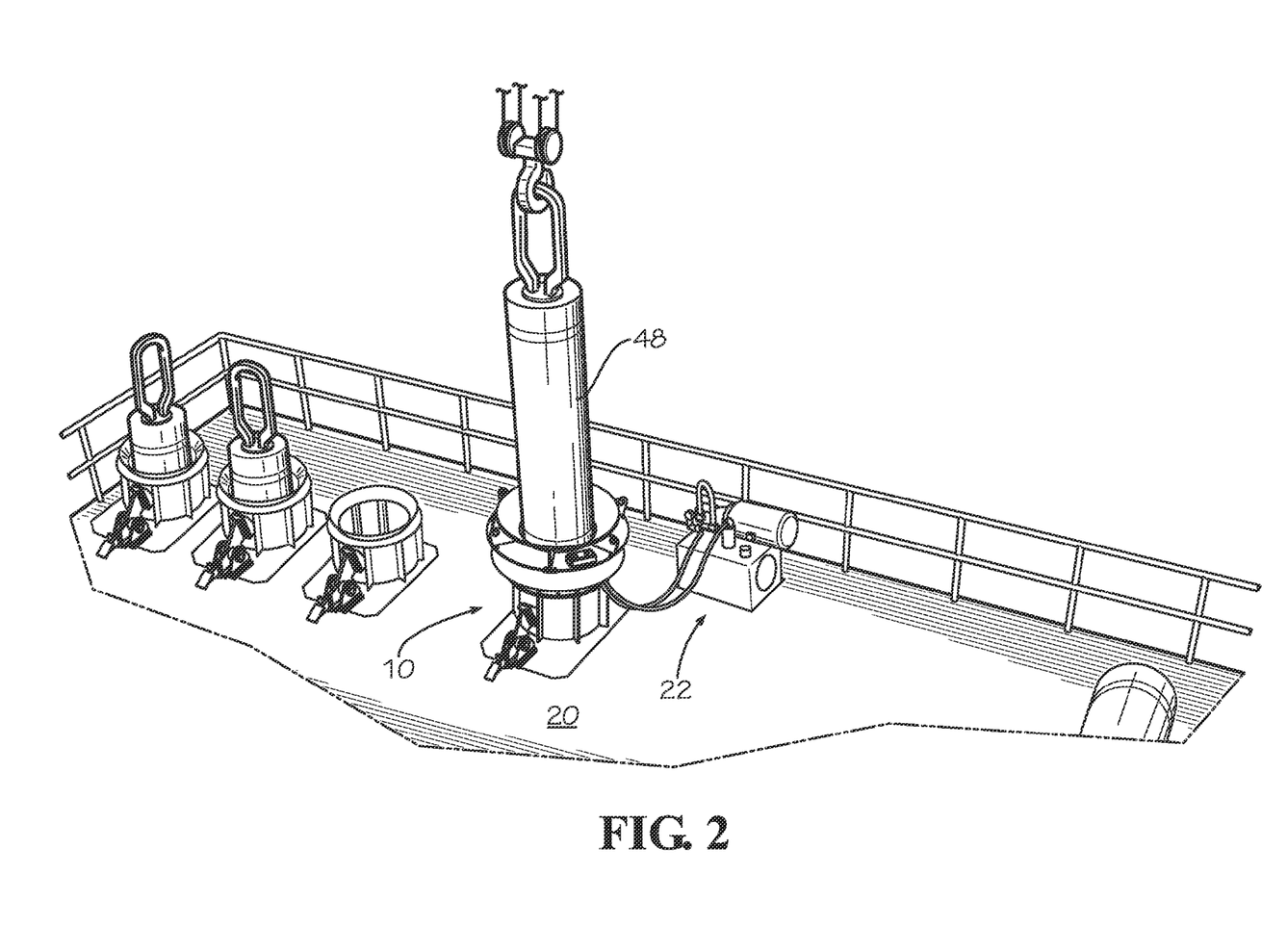
FIG. 2 is a perspective view of an embodiment of an electrode joining apparatus including a first electrode positioned for lowering into an electrode holder.
Figure 3:
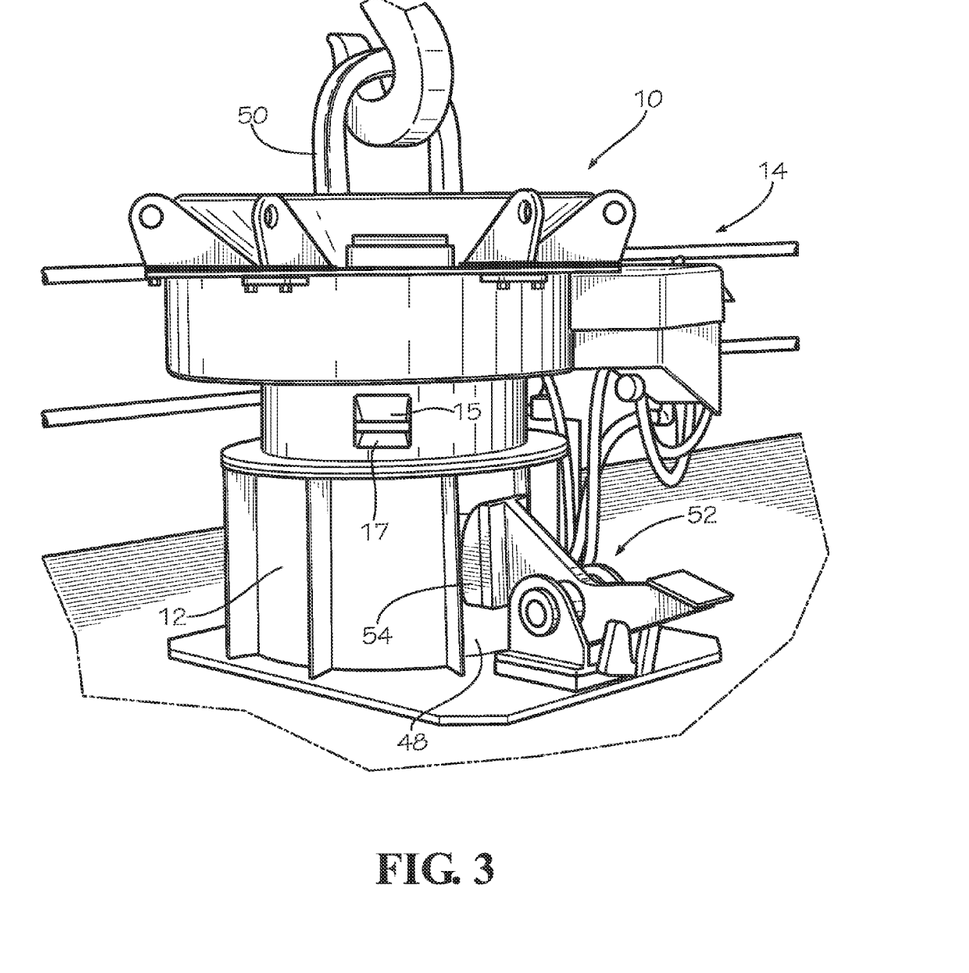
FIG. 3 is a perspective view of an embodiment of an electrode joining apparatus including a first electrode disposed in an electrode holder.

Referring to FIG. 2, an electrode joining device 10 is positioned on a platform in some embodiments. To join two electrodes together, a first electrode 48 may be loaded into electrode joining device 10 from above. The first electrode 48 is lowered downwardly through the apparatus 10 and through the hole 56 in the platform from above using an overhead crane in some applications. As seen in FIG. 3, the first electrode 48 is lowered to a point where the majority of the electrode has passed through the torque device 14. A window 15 in the riser portion of the torque device allows visual inspection of the location of the upper edge of the first electrode 48 in some applications. Once vertically positioned, a latch 52 on the electrode holder 12 may be actuated to lower a holder grip 54, as seen in FIG. 3. The holder grip 54 engages the upper end of the first electrode 48, thereby fixing the first electrode 48 in place. As such, first electrode 48 becomes a fixed electrode. The electrode holder 12 locks the fixed electrode in place and prevents both rotation and axial displacement of the fixed electrode. In this position, the top end 17 of the fixed electrode may be positioned inside the torque device as seen through window 15.

From this position the lift device 50 can be unscrewed from the top of the fixed electrode to reveal a threaded region on the fixed electrode for receiving a corresponding threaded region on a second electrode. When lift device 50 is removed, a vacant space on the interior of the torque device 14 is configured to receive a lower end of a free electrode.

Figure 4:
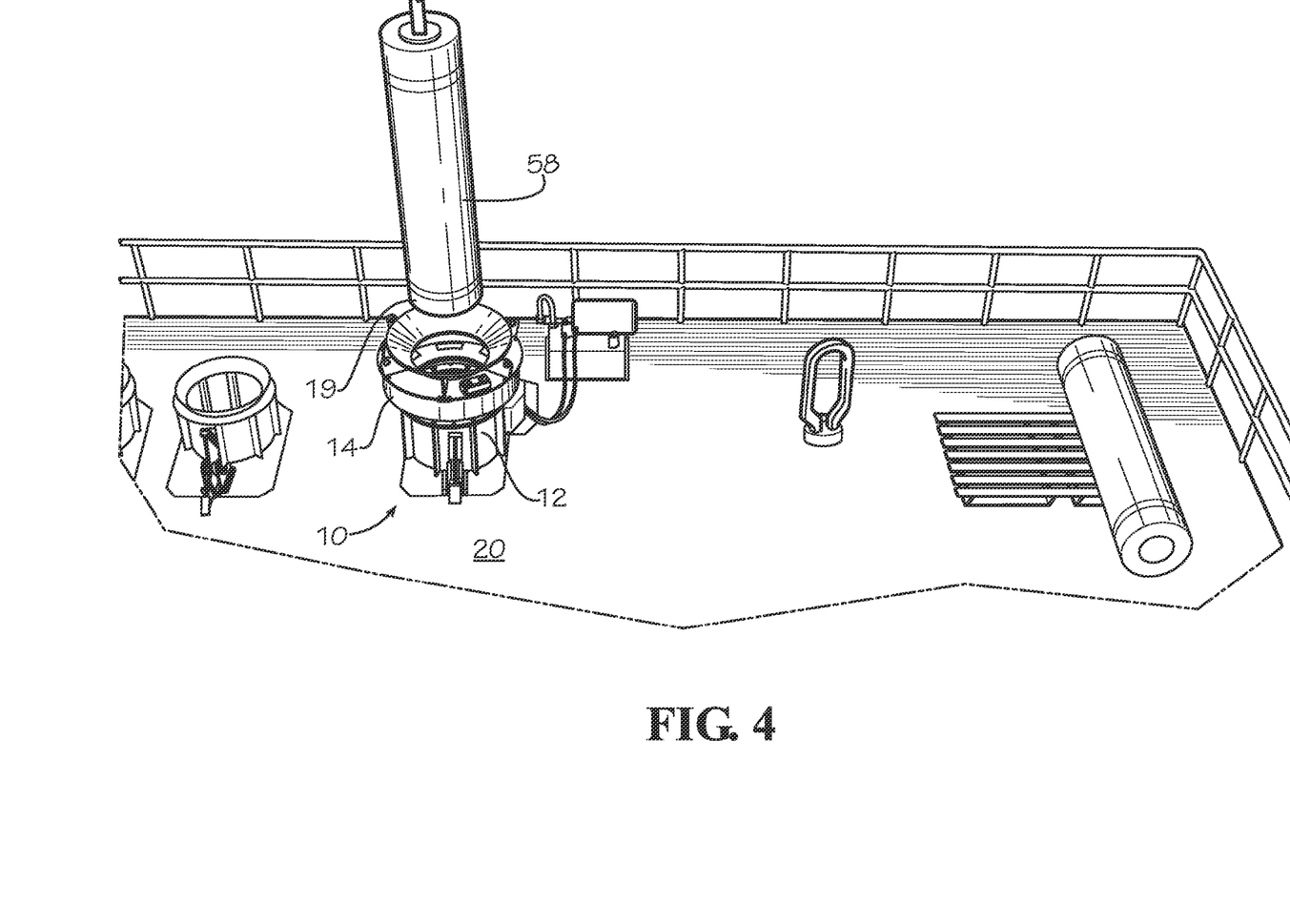
FIG. 4 is a perspective view of an embodiment of an electrode joining apparatus including a second electrode positioned for lowering into a torque device above an electrode holder suspending a first electrode.

As seen in FIG. 4, a second electrode 58 may be loaded from a horizontal position to be installed vertically into the joining device 10. The second electrode 58 is lifted to a vertical orientation as seen in FIG. 4. The lower end 19 of the second electrode 58 is lowered into the torque device 14 to a position above the upper end of the fixed electrode. The lower end of the second electrode 58 is positioned a predetermined gap distance above the upper end of the fixed electrode. The gap distance is provided to ensure delicate threads do not inadvertently damage corresponding threads on the adjacent electrode. When a desired gap distance is reached, the system is ready to begin the spin-down stage of free electrode rotation. The gap distance may be observed through window 15, and a spacer may be used between the electrode ends to ensure adequate spacing prior to rotation of the free electrode.

After the free electrode is positioned above the fixed electrode, torque device 14 is operated to engage the free electrode and rotate the free electrode relative to the fixed electrode. Once the ends of the electrodes make contact during spin-down, the second torque stage is entered, and applied force is increased until a value corresponding to a desired torque is reached. The joined electrodes remain fixed in place due to the engagement of the holder grip of the electrode holder engaging the fixed electrode. After joining, the joined electrode may be removed as a single multi-section electrode assembly.

During both the spin-down and the torque stages of free electrode rotation, a lift device such as a lift plug or a clamp may remain attached to the upper end of the free electrode. However, after proper torque is achieved, the lift device may be removed and replaced with another lift device if necessary, and the joined electrode may be lifted out of the joining device 10 and moved to a furnace for use.

Figure 5:
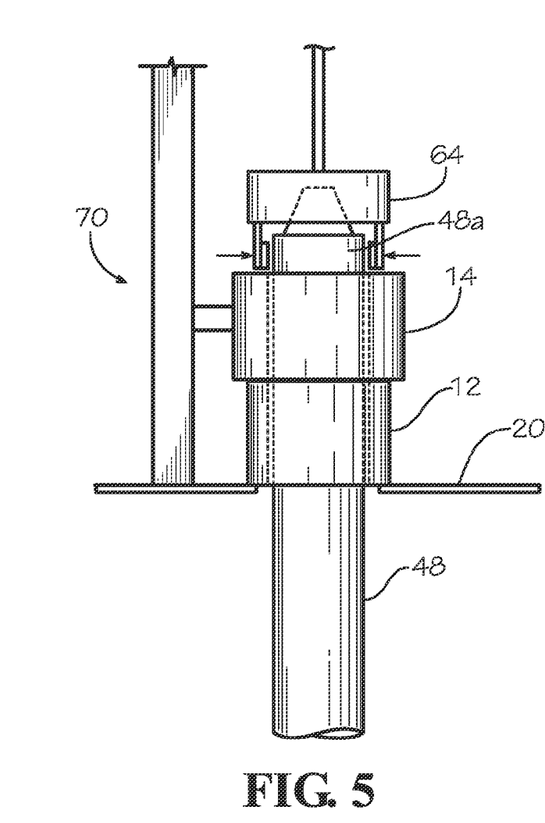
FIG. 5 illustrates a schematic of an electrode joining apparatus including a torque device attached to a lift.

As noted above, when the first electrode is lowered into the torque device 14 using a lift plug, the top end of the first electrode may be lowered vertically below the upper end of the funnel 16 because the lift plug has a sufficient diameter to fit inside the axial passage in the torque device 14. However, other graphite electrode handling equipment that may be used to lower the first electrode will not fit inside the axial passage. For example, as seen in FIG. 5, a second type of graphite electrode lifting device 64 includes an outer diameter greater than the inner diameter of the axial passage in torque device 14. As such, the lifting device 64 may not be lowered below funnel 16. A lifting device 64 such as this may apply a clamping force to the outer side surface of an electrode to lift the electrode, acting as a tong or clamp against the electrode surface. Lifting devices that apply a clamping force against the surface of an electrode are often needed to lift graphite electrodes that include a threaded male fitting at the upper end of the electrode instead of a female threaded socket. However, in some embodiments, lifting devices that apply a clamping force against the side surface of an electrode may also be used to lift graphite electrodes that include female threaded sockets at the upper end.

As seen in FIG. 5 in some embodiments, after the first electrode 48 is lowered into the torque device 14 and electrode holder 12 and locked in place using the holder grip on the electrode holder, an upper end 48*a* of first electrode 48 extends above torque device 14. In such a configuration, the grippers on the inside of torque device 14 are not positioned to engage a section of a second electrode. As a result, the torque device 14 cannot be used to apply torque against a second free electrode introduced from above. Additionally, once the first electrode 48 is installed and held in place with the holder grip 54 on electrode holder 12, it is nearly impossible to release the holder grip and adjust the vertical position of the first electrode 48 after the lifting device 64 has been detached from the electrode.

Figure 6:
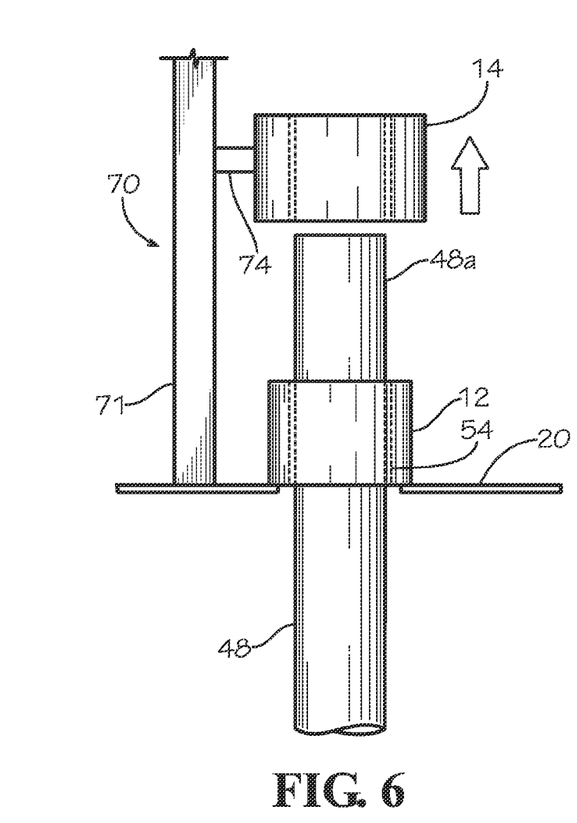
FIG. 6 illustrates a schematic of an electrode joining apparatus including a torque device raised above an electrode holder using a lift, the electrode holder having a first electrode fixed in the electrode holder.

To overcome this problem, the present disclosure provides an electrode joining apparatus including a base, or platform 20, an electrode holder 12 on the base, a torque device 14 positioned above the base 12, and a lift 70 for selectively raising or lowering the torque device 14 relative to the electrode holder 12. Torque device 14 is mounted to lift 70, such that torque device 14 may be raised up toward the upper free end 48*a* of the fixed electrode, as shown in FIG. 6. Lift 70 includes various embodiments capable of raising torque device 14 generally vertically above electrode holder 12. Lift 70 may include any suitable device for lifting torque device 14 above electrode holder 12. In some embodiments, lift 70 includes one or more vertical rails 71 or masts extending upwardly from base 20 beside the electrode holder. Each rail or mast may be mounted to the platform 20 using bolts or fasteners in some embodiments. A moveable carriage 74 is installed on the rail or rails, or mast, in some embodiments. Torque device 14 is attached to the carriage 74. Torque device 14 may be attached to carriage 74 either directly or indirectly. During use, carriage 74 is movable along the rail or mast, allowing torque device 14 to be moved relative to electrode holder 12.

Figure 7:
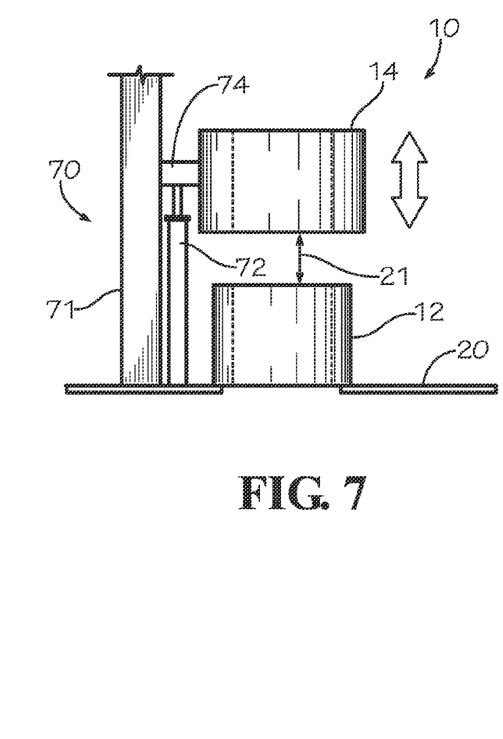
FIG. 7 illustrates a schematic of an electrode joining apparatus including a torque device raised above an electrode holder using a lift.

As shown in FIG. 7, carriage 74 is raised and lowered using a powered drive 72 such as a pneumatic or hydraulic drive in some embodiments. In other embodiments, lift 70 may be powered using a cable drive, electric gear drive, or any other suitable drive for raising or lowering carriage 74. In some embodiments, one drive 72 is operable to provide both raising and lowering of carriage 74 in a controlled manner. In other embodiments, a first drive is operable to raise carriage 74, and a second drive is operable to lower carriage 74.

When the torque device 14 is raised or lowered relative to electrode holder 12, a variable gap 21 is provided between torque device 14 and electrode holder 12, as seen in FIG. 7. An electrode joining station having a torque device that can be raised and/or lowered relative to the electrode holder is different from conventional electrode joining station that includes a fixed spacing or fixed connection between the lower end of the torque device 14 and the upper end of the electrode holder 12.

Figure 8:
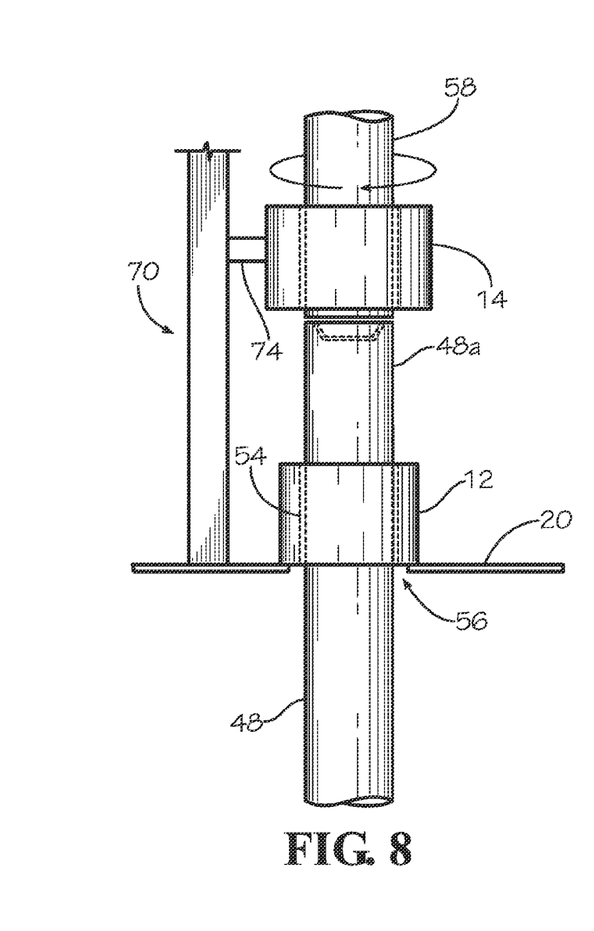
FIG. 8 illustrates a schematic of an electrode joining apparatus including a torque device raised above an electrode holder using a lift, including a first electrode fixed in the electrode holder and a second electrode axially received in the torque device above the first electrode.
Figure 9:
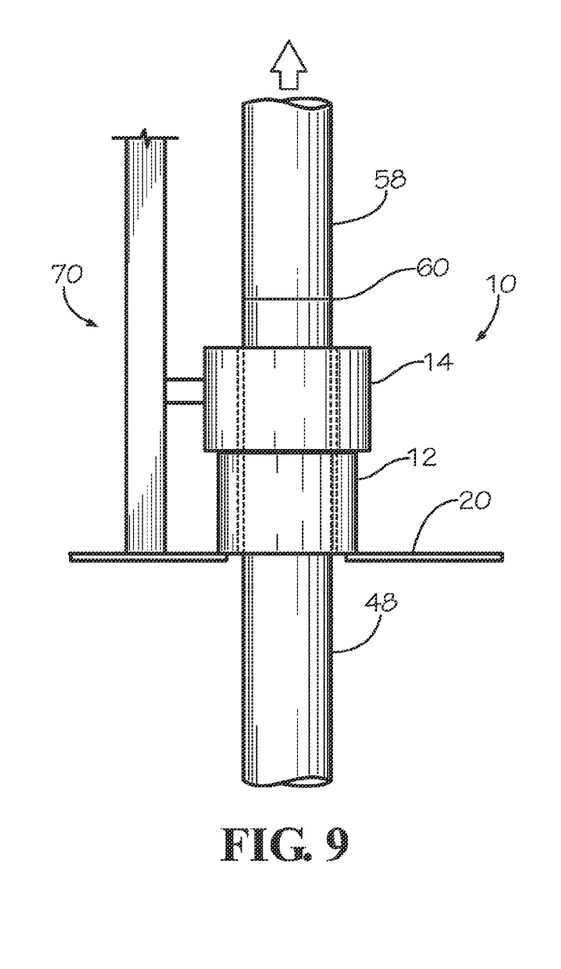
FIG. 9 illustrates a schematic of an electrode joining apparatus including a torque device attached to a lift and a joined electrode positioned for vertical removal from the device.

During use, as seen in FIG. 4, a user may install the first electrode 48 in the electrode holder 12 and lock it in place. Torque device 14 may subsequently be raised to a suitable position relative to the upper end of the first electrode 48, as seen in FIG. 6. A second electrode may then be positioned over the torque device and lowered down into the axial passage to an appropriate spacing relative to the top end of the fixed electrode, as shown in FIG. 8. In some applications the spacing between the lower end of the free electrode and the upper end of the fixed electrode is set using a gap spacer. Torque device 14 may then be operated while maintained in the raised position to engage the lower end of the free electrode 58 for the spin-down and/or torque stage as shown in FIG. 8. Once the torque stage is complete, the torque device grippers are disengaged from the electrode, and the torque device may be lowered. The electrode sections are then joined at joint 60, as seen in FIG. 9. The joined electrode may then be raised vertically out of the torque device using an overhead lifting device for transfer to a furnace for use.

As shown in FIG. 8, in some embodiments, electrode joining apparatus 10 includes a platform 20 defining a platform opening 56. A first electrode 58 is lowered into the electrode holder 12 from above and is locked into place using one or more grips 54 applying a force against the side wall of the electrode. As such, the first electrode 48 may be suspended partially below platform 20, and a free end 48*a* of first electrode 48 protrudes above electrode holder 12. As shown in FIG. 8, in some embodiments, upper free end 48*a* of first electrode 48 includes a female socket defined in its upper free end. The female socket is tapered and threaded in some embodiments to accept a corresponding tapered and threaded male connector on another electrode for establishing a threaded joint. As seen in FIG. 8, a second electrode 58 is lowered toward the first electrode 48 from above, such that the male connector on the second electrode partially fills the socket on the first electrode. Once the second electrode is lowered to the desired position, the torque device may be engaged to rotate the second electrode, causing threads on the corresponding features to engage and to establish a threaded joint.

Figure 10:
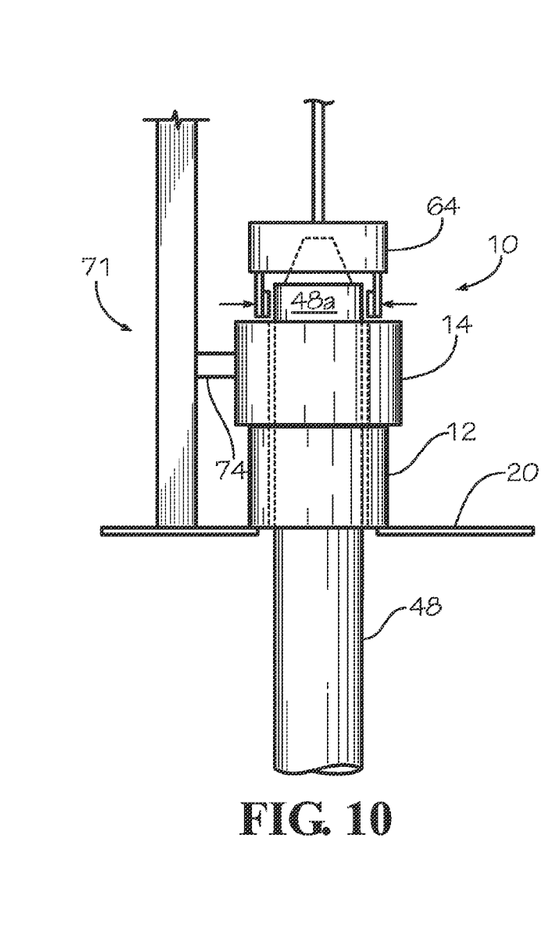
FIG. 10 illustrates a schematic of an electrode joining apparatus including a torque device positioned above an electrode holder and including a first electrode axially lowered into the apparatus using an electrode lifting device.

In other embodiments, electrode joining device 10 is operable to join a different type of first electrode 48 having a male connector at its upper end 48*a*. As seen in FIG. 10, in some embodiments, first electrode 48 includes an upper end 48*a* including a tapered and threaded male extension, or male connector. In such embodiments, first electrode 48 is lowered into position using an electrode lifting device 64. One benefit of the electrode joining apparatus 10 including an electrode holder, a torque device, and a lift operable to raise the torque device relative to the electrode holder is the ability of apparatus 10 to facilitate joining of electrodes having upper end male connectors. Some commercial graphite electrode manufacturers include graphite electrodes having male connectors on the upper electrode ends. Other commercial graphite electrode manufacturers produce graphite electrodes having female sockets on the upper electrode ends. Some conventional electrode joining devices including a torque device fixed to an electrode holder do not allow for joining electrodes having male connectors on upper electrode ends due to clearance issues within or near the torque device required for the types of lifting devices that are capable of vertically lifting those types of electrodes. However, by providing an electrode joining device 10 with a lift operable to raise the torque device 14 above the electrode holder 12, it is possible to join both types of electrodes in various embodiments.

Figure 11:
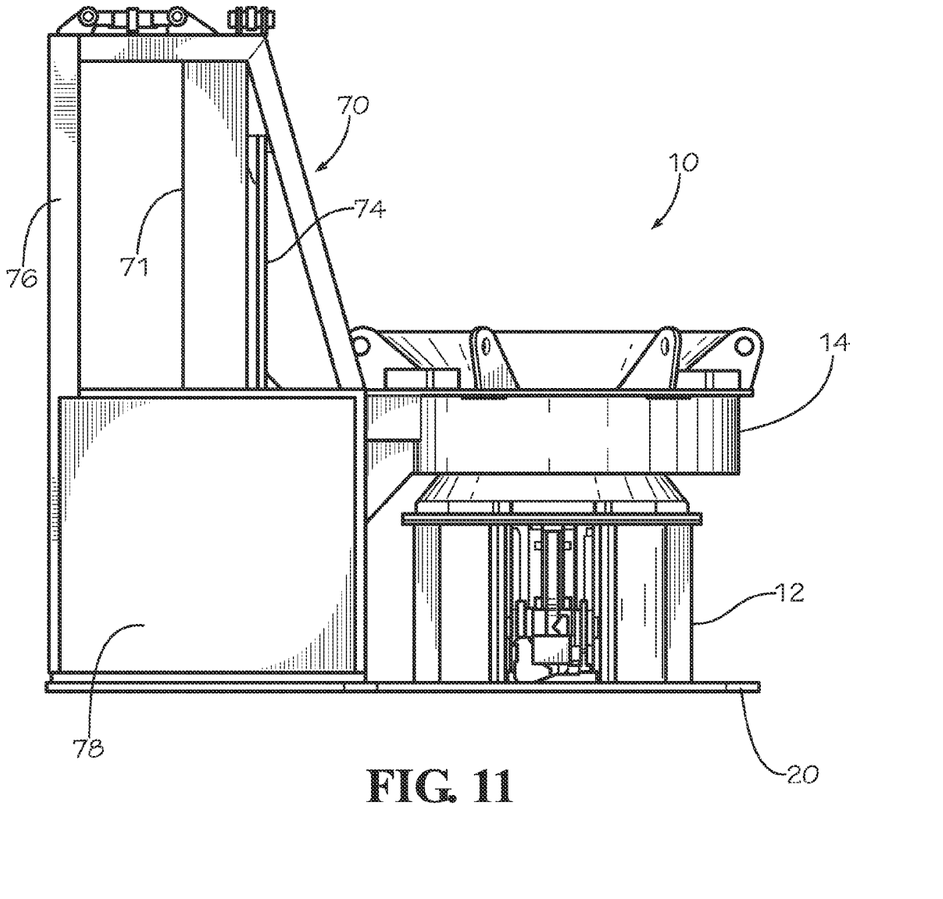
FIG. 11 illustrates a schematic of an electrode joining apparatus including a torque device positioned above an electrode holder and including a lift operable to raise the torque device above the electrode holder.
Figure 12:
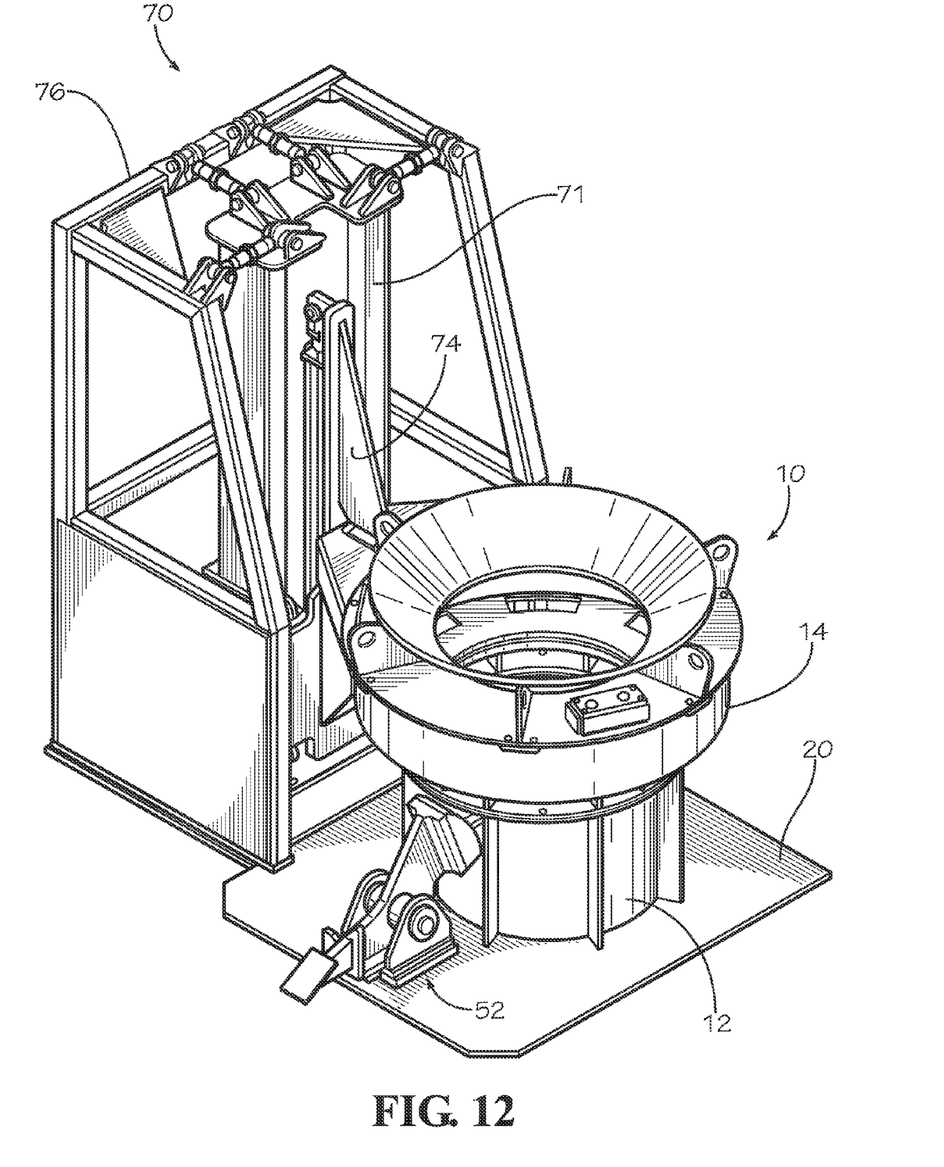
FIG. 12 illustrates a schematic of an electrode joining apparatus including a torque device positioned above an electrode holder including a lift operable to raise the torque device above the electrode holder.

Electrode joining device 10 in some embodiments includes an electrode holder having an axial passage positioned to accept an electrode, a torque device positioned above the electrode holder including an axial passage positioned to accept a second electrode, and a lift including a carriage, wherein the torque device is attached to the carriage. The carriage is vertically moveable on the lift to allow the torque device to be raised above the electrode holder. Referring to FIGS. 11 and 12, in some embodiments, lift 70 includes a carriage 74 positioned on a mast or a tower 71. In some embodiments, mast 71 includes one or more rails. Torque device 14 is cantilevered from carriage 74 as the carriage moves up and down along the mast 71. Electrode holder 12 remains fixed to platform 20, allowing latch 52 to be engaged to secure a fixed electrode suspended below platform 20 during use. In some embodiments, a frame 76 is disposed around mast 71 to provide additional rigidity for mast 71. Because torque device 14 is cantilevered, a moment is applied to mast 71 during use. Frame 76 is coupled to the upper end of mast 71 in some embodiments to prevent undesired flexing or bending of mast 71 during use.

As seen in FIGS. 11 and 12, in some embodiments, a cage or shield 78 may be installed around the carriage and/or mast to avoid outside objects from becoming entangled in the device. Shield 78 further provides protection for workers to prevent body parts from entering the space where the carriage moves.

Figure 13:
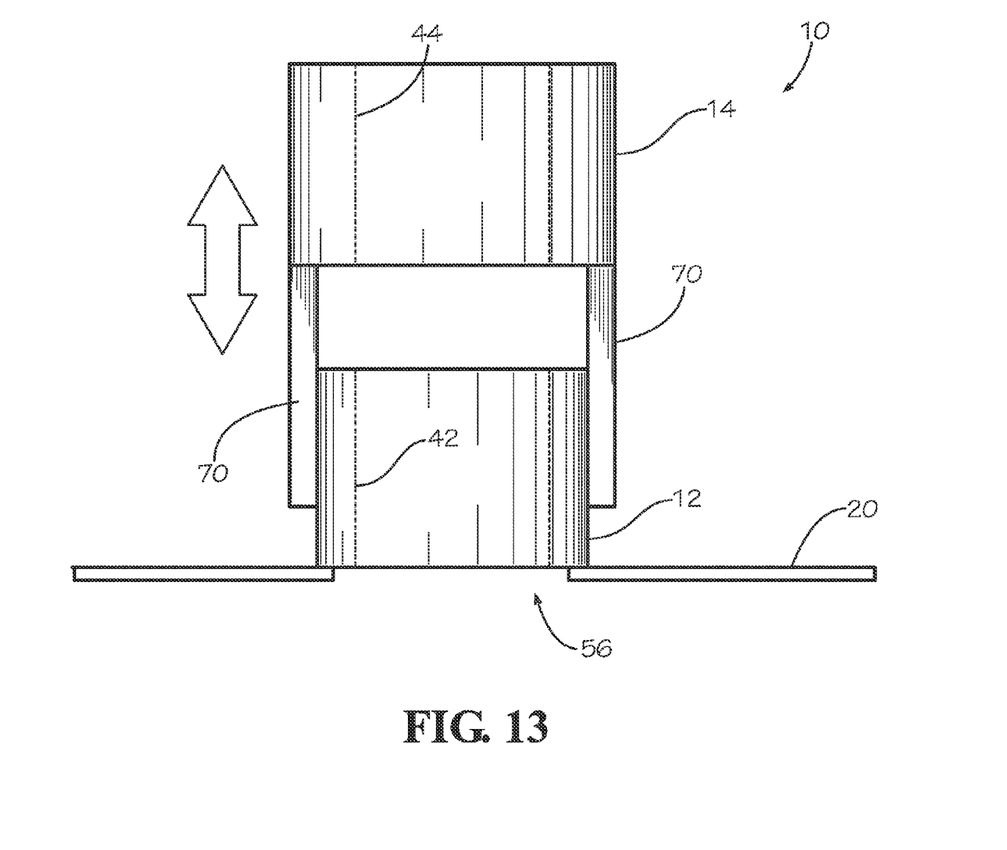
FIG. 13 illustrates a schematic of an electrode joining apparatus including a torque device positioned above an electrode holder and a lift disposed between the electrode holder and the torque device operable to raise the lift relative to the torque device.

Referring to FIG. 13, in some embodiments, electrode joining device 10 includes an electrode holder 12 and a torque device 14 positioned above the electrode holder 12. Electrode holder 12 includes a first axial passage 42 configured to receive a first electrode, and torque device 14 includes a second axial passage 44 configured to receive a second electrode. A lift 70 is disposed between the electrode holder 12 and the torque device 14. Lift 70 is operable to raise the torque device 14 relative to the electrode holder 12. In some embodiments, first axial passage 42 and second axial passage 44 are co-axially aligned. Lift 70 is operable to raise and lower the torque device 14 relative to electrode holder 12 in some embodiments. Lift 70 includes one or more powered actuators in some embodiments. Each powered actuator on lift 70 is operable to provide force to mechanically lift torque device 14 above electrode holder 12. The powered actuators on lift 70 may include pneumatic actuators, hydraulic actuators, mechanical actuators, or other actuators operable to move torque device 14 relative to electrode holder 12.

Thus, although there have been described particular embodiments of the present invention of a new and useful Electrode Joining Apparatus with Torque Device Lift, it is not intended that such references be construed as limitations upon the scope of this invention.

What is claimed is:

1. An electrode joining apparatus for joining a first electrode and a second electrode, comprising:
    an electrode holder including a first axial passage shaped to receive the first electrode;
    a torque device positioned above the electrode holder, the torque device configured to selectively rotate the second electrode relative to the first electrode, the torque device including a second axial passage shaped to receive the second electrode, wherein the first and second axial passages are co-axial;
    a lift including a vertically moveable carriage, wherein the torque device is attached to the carriage, and the carriage is operable to move the torque device vertically relative to the electrode holder; and
    a vertical mast on the lift, wherein the carriage is vertically moveable along the mast.

2. The apparatus of claim 1, further comprising:
    a platform, the electrode holder mounted on the platform; and
    a hole defined in the platform below the electrode holder.

3. The apparatus of claim 2, wherein the first axial passage in the electrode holder is open to the hole such that the first electrode may extend downwardly through the first axial passage and the hole when inserted into the electrode holder.

4. The apparatus of claim 3, wherein the electrode holder is fixed to the platform.

5. The apparatus of claim 4, wherein the lift is fixed to the platform.

6. The apparatus of claim 5, further comprising a powered actuator on the lift, the powered actuator positioned to selectively move the carriage relative to the platform.

\* \* \* \* \*